US00PP27184P2

(12) United States Plant Patent
Kordes

(10) Patent No.: US PP27,184 P2
(45) Date of Patent: Sep. 27, 2016

(54) SHRUB ROSE PLANT NAMED 'KORGLOJAKA'

(50) Latin Name: *Rosa hybrida*
Varietal Denomination: KORglojaka

(71) Applicant: Tim-Hermann Kordes, Klein Offenseth-Sparrieshoop (DE)

(72) Inventor: Tim-Hermann Kordes, Klein Offenseth-Sparrieshoop (DE)

(73) Assignee: W. Kordes Sohne Rosenschulen Gmbh & Co. KG, Offenseth-Sparrieshoop (DE)

( * ) Notice: Subject to any disclaimer, the term of this patent is extended or adjusted under 35 U.S.C. 154(b) by 116 days.

(21) Appl. No.: 14/120,939

(22) Filed: Jul. 11, 2014

(51) Int. Cl.
*A01H 5/00* (2006.01)

(52) U.S. Cl.
USPC ..... Plt./107

(58) Field of Classification Search
USPC ..... Plt./107, 102
See application file for complete search history.

(56) References Cited

PUBLICATIONS

PLUTO Plant Variety Database Dec. 16, 2015.*

* cited by examiner

*Primary Examiner* — Annette Para

(57) ABSTRACT

A new and distinct variety of rose with long lasting, novel soft pink flowers, and attractive foliage with very good disease resistance. It exhibits bushy to upright growth with abundant flowers. The new variety propagates well from cuttings and by grafting. This new and distinct variety has shown to be uniform and stable in the resulting generations from asexual propagation.

1 Drawing Sheet

Latin name of genus and species: The botanical classification of the new rose plant is *Rosa hybrida.*

Variety denomination: The denomination of the new variety is 'KORglojaka'.

CROSS REFERENCES AND FEDERAL R&D STATEMENT

There are no cross referenced or related applications. This variety was developed without the aid of any research grant.

BACKGROUND OF THE INVENTION

The new variety of rose plant of the present invention originated from a controlled crossing in a breeding program of two distinct parents during the summer of 2002. The crossing was between an un-named seedling, the seed parent, and another un-named seedling, the pollen parent by the same inventor.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORglojaka'.

SUMMARY OF THE INVENTION

The new rose plant may be distinguished from its seed parent, an un-named seedling, by the following combination of characteristics:

1. 'KORglojaka' has soft pink flowers , whereas the un-named seedling has violet pink flowers.

2. 'KORglojaka' has very good disease resistance, whereas the un-named seedling has average disease resistance.

The new rose plant may be distinguished from its pollen parent, an un-named seedling, by the following combination of characteristics:

1. 'KORglojaka' has large flowers, whereas the un-named seedling has medium flowers.
2. 'KORglojaka' has a very double petal count, whereas the un-named seedling has a semi-double petal count.

The objective of the hybridization was to create a new and distinct rose plant with unique qualities, such as:

1. Uniform growth and flowering;
2. Abundant attractive, recurrent flowers;
3. Attractive and abundant foliage; and
4. Resistance to diseases encountered in landscapes and gardens.

This combination of qualities is not present in prior rose cultivars known to the inventor. These objectives have been substantially achieved and in that distinguish 'KORglojaka' from all other varieties of which I am aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORglojaka' was selected in May 2003 from the seedling beds to be asexually propagated for further evaluation. The first asexual propagation of 'KORglojaka' was done by budding in July 2003 at the inventor's nursery in Offenseth-Sparrieshoop, Germany.

These initial and other subsequent propagations conducted in controlled environments demonstrate that 'KORglojaka' reproduces true to type in successive generations of asexual reproduction.

BRIEF DESCRIPTION OF THE DRAWING

The accompanying color drawing shows as true as is reasonably possible to obtain in color photographs of this type, the typical characteristics of the buds, sepals, reproductive organs, flowers, leaves, prickles, and stems of 'KORglojaka'.

DETAILED BOTANICAL DESCRIPTION

The following is a description of 'KORglojaka', as observed growing in May 2014 in a nursery in Jackson County, Oreg. on plants of 3 years of age. Color references are made using The Royal Horticultural Society (London, England) Colour Chart, 2001 except where common terms of color are used.

For a comparison, several physical characteristics of the rose variety 'KORparofe', a rose variety from the same inventor described and illustrated in U.S. Plant Pat. No. 21,529 issued on Nov. 30, 2010 are compared to 'KORglojaka' in Chart 1.

CHART 1

| Characteristic | 'KORglojaka' | 'KORparofe' |
|---|---|---|
| Fragrance. | None. | Strong. |
| Average number of stamens. | Approximately 120. | Approximately 10 to 20. |
| Petal count under normal conditions. | Approximately 55 to 65. | Approximately 90 to 110. |

Parents:

*Seed parent*.—An un-named seedling.

*Pollen parent*.—An un-named seedling.

Classification:

*Botanical classification*.—*Rosa hybrida* 'KORglojaka'.

*Commercial classification*.—Shrub rose.

FLOWER AND FLOWER BUD

Blooming habit: Recurrent.

Flower bud:

*Size*.—Upon opening, 40 mm in length from base of receptacle to distal end of bud and 30 mm diameter at its widest point.

*Bud form*.—Short. Globular.

*Bud color*.—As sepals first unfold, bud color is Red-Purple Group 61B with intonations of Yellow-Green Group 145C. When ¼ open, the upper surface of petals is White Group 155C with intonations of Red-Purple Group 61C on the margin, and the lower surface is White Group N155D with intonations of Red-Purple Group 61C in the middle zone and the marginal zone. The outermost petals are Red-Purple Group 61A to C, with intonations of Yellow-Green Group 145D in the basal zone, and Yellow Group 146C along the midrib.

*Sepals*.—Color: Upper surface Yellow-Green Group 144A. Lower surface Yellow-Green Group 144A. Occasional intonations of Red-Purple Group 61B in the middle zone and the marginal zone. Size: Average 20 to 25 mm (l)×7 mm (w). Shape: Weak foliaceous appendages on several of the sepals. Apex: Apiculate. Base: Flat at union with receptacle. Quantity: Five. Surface texture: Upper side: Silky. Strongly pubescent. Lower surface: Leathery. Pubescent. Margins: Ciliate. Stipitate glands: Limited, on margins.

Flower bloom:

*Fragrance*.—None.

*Duration*.—On the plant 6 to 8 days. Senesced petals drop away cleanly.

*Size*.—Large for a shrub rose. When open, the average flower diameter is 80 to 95 mm and the average flower height is 35 to 40 mm.

*Form*.—Shape of flower when viewed from the side: Upon opening, upper part: Flat. Upon opening, lower part: Flat. Open flower, upper part: Flat. Open flower, lower part: Concave.

Color:

*Upon opening, petals*.—Outermost petals: Outer Side: Red-Purple Group 65C, with intonations of Red-Purple Group 61D in the marginal zone. Inner Side: White Group 155D, with intonations of Red-Purple Group 61C on in the marginal zone. Innermost petals: Outer Side: White Group 155D, with Orange group 27D in the basal zone. Inner Side: Yellow-White Group 158, with Yellow Group 8D in the basal zone.

*Upon opening, basal petal spots*.—Basal petal spot, outermost petals: Outer Side: Yellow Group 3C. Inner Side: Yellow Group 3C. Basal petal spot, innermost petals: Outer Side: Yellow Group 7D. Inner Side: Yellow Group 8A.

*After opening, petals*.—Outermost Petals: Outer Side: White Group N155B, with intonations of Red-Purple Group N57C in the marginal zone. Inner Side: White Group N155B, with intonations of Red-Purple Group N57C in the marginal zone. Innermost petals: Outer Side: White Group 155B in the basal and middle zones, Red-Purple Group N57C in the marginal zone. Inner Side: White Group 155B in the basal and middle zones, Red-Purple Group N57C in the marginal zone.

*After opening, basal petal spots*.—Basal petal spot, outermost petals: Outer Side: Yellow Group 3C. Inner Side: Yellow Group 3C. Basal petal spot, innermost petals: Outer Side: Yellow Group 4D. Inner Side: Yellow Group 4D.

General tonality: On open flower Red-Purple Group 62D. No change in the general tonality at the end of the 4th day. Afterwards, general tonality is White Group 155C.

Petals:

*Petal count*.—Very Double.

*Average range*.—Approximately 55 to 65 petals under normal conditions.

*Petal reflex*.—Moderate.

*Petal margin*.—Entire to ruffled.

*Petal shape*.—Obovate. Apex: Obtuse. Base: Cuneate.

*Petal size*.—Outermost Petals: 50 mm (l)×50 mm (w). Innermost Petals: 27 mm (l)×27 mm (w).

*Petal arrangement*.—Formal.

*Texture*.—Smooth.

Petaloids:

*Petaloid count*.—Average of 15 to 18 per flower.

*Petaloid size*.—Variable. 8 to 25 mm (l)×5 to 20 mm (w).

*Petaloid color*.—Inner side: White Group 155C in the basal zone, Red-Purple Group 69A in the middle and marginal zones. Outer side: White Group 155C in the basal zone, Red-Purple Group 69A in the middle and marginal zones.

*Petaloid texture*.—Silky.

*Margins*.—Undulated to indented.

*Petaloid shape*.—Variable. Most commonly obovate to oblong. Apex: Obtuse to emarginate. Base: Cuneate to attenuate.

Reproductive organs:

*Pistils*.—Abundant. Approximately 80 present. Stigmas: Location: Equal to or slightly inferior in position to the anthers. Color: Greyed-Yellow Group 162B. Styles: Length: About 5 to 10 mm long. Color: Yellow Group 10D with intonations of Red-Purple Group N57A at apex.

*Stamens*.—Approximately 120 on average and regularly arranged. Anthers: Size: Average 2 mm (l)×1 mm (w). Pollen: Generally present. Color: Greyed-Orange Group 163B to Greyed-Orange Group 165B. Filaments: Color: Yellow Group 10B. Length: 5 to 8 mm.

*Receptacle*.—Surface: Glossy. Color: Yellow-Green Group 144A with intonations of Greyed-Purple Group 183A. Shape: Urn-shaped. Texture: Smooth, slightly pubescent. Size: 8 mm (h)×10 mm (w).

*Pedicel*.—Surface: With limited numbers of stipitate glands. Length: 55 to 65 mm average length. Diameter: 2.5 to 3.5 mm average diameter. Color: Yellow-Green Group 144B to 144C. Strength: Somewhat strong. Texture: Glabrous. Borne: Multiple flower buds per stem, generally 1 to 6. Flowers held upright.

*Peduncle*.—Surface: Glabrous. Length: 60 to 120 mm average length. Diameter: 3 to 5 mm average diameter. Color: Yellow-Green Group 144B, with slight intonations of Greyed-Purple Group 184B. Strength: Strong. Borne: Multiple flower buds per stem, generally 1 to 6. Flowers held upright.

THE PLANT

Growth: Moderately vigorous.

Plant habit: Bushy to upright. When grown as a field plant, the average plant height is 135 cm and the average plant width is 75 cm.

*Stems*.—Stem color: Young wood: Yellow-Green Group 144B. Older wood: Yellow-Green Group 144A. Intonations: Greyed-Purple Group 184D. More strongly present on younger wood. Stem surface texture: Young wood: Smooth. Older wood: Smooth.

*Prickles*.—Present on older wood. Incidence: Average of 5 to 10 per each 10 cm of stem. Size: Average length: 5 to 10 mm.. Color: Immature prickles: Yellow-Green Group 145C. Mature prickles: Yellow-Green Group 145C. Shape: Concave. Anthocyanin: Observed on all prickles. Color: Greyed-Purple Group 184A.

*Leaves*.—Normally 5 leaflets on normal leaves in middle of the stem. Venation pattern: Pyramidal net pattern. Leaf size: 120 to 155 mm (l)×90 to 120 mm (w). Abundance: Average.

*Leaflets*.—Size: Average size of the terminal leaflet is 65 mm (l)×45 mm (w). Shape: Elliptic. Base: Obtuse. Apex: Acute. Margins: Serrated. Surface: Upper: Semi-glossy. Lower: Matte. Texture: Upper side of leaflet: Leathery. Under side of leaflet: Leathery. Color, mature foliage: Upper Leaflet Surface: Green Group 137A. Lower Leaflet Surface: Yellow-Green Group 146B. Color, juvenile foliage: Upper Leaflet Surface: Yellow-Green Group 146B. Lower Leaflet Surface: Yellow-Green Group 146B. Anthocyanin intonations Greyed-Purple Group 183B. Arrangement: Odd pinnate. Venation: Reticulate.

*Stipules*.—Size: 20 to 25 mm (l)×6 to 8 mm (w). Stipule color: Yellow-Green Group 146B and 146C. Anthocyanin: Greyed-Purple Group 185C. Stipitate glands: Abundant on margins. Margins: Pectinate. Texture: Smooth, slightly pubescent. Shape: Apex: Apiculate. Base: Flat.

*Petiole*.—Length: Average 35 to 50 mm. Diameter: Average 1.5 mm. Petiole color: Upper Surface: Yellow-Green Group 146A on the margins, Yellow-Green Group 144C on the midrib. Underneath: Yellow-Green Group 144B. Margins: With stipitate glands. Anthocyanin: Greyed-Purple Group 185C. Present on midrib, underside and prickles. Prickles: 1 to 3 small prickles present on underside. Stipitate Glands: Limited, present on margins only. Texture: Glabrous.

*Petiole rachis*.—Length: Average 15 to 20 mm. Diameter: Average 1 to 1.5 mm. Color: Yellow-Green Group 146C. Anthocyanin: Greyed Purple Group 185C. Present on midrib, margins and underside. Margins: Stipitate glands present. Prickles: A few small prickles underneath. Stipitate glands: Limited number of stipitate glands on margins.

Hips/seed formation: On mature stems. Sepals persisting.

*Surface*.—Glossy.

*Color*.—Yellow-Green Group 144A with intonations of Greyed-Purple Group 183A.

*Shape*.—Ovate.

*Texture*.—Smooth, slightly pubescent.

*Size*.—15-17 mm (h)×10-12 mm (w).

Winter hardiness: To date, the variety has been grown successfully in Zone 6.

Disease resistance: Very good resistance to Powdery mildew (*Sphaerotheca pannosa*) and blackspot (*Diplocarpon rosae*) diseases under normal growing conditions in Jackson County, Oreg.

I claim:

1. A new and distinct variety of rose plant, as described and illustrated herein.

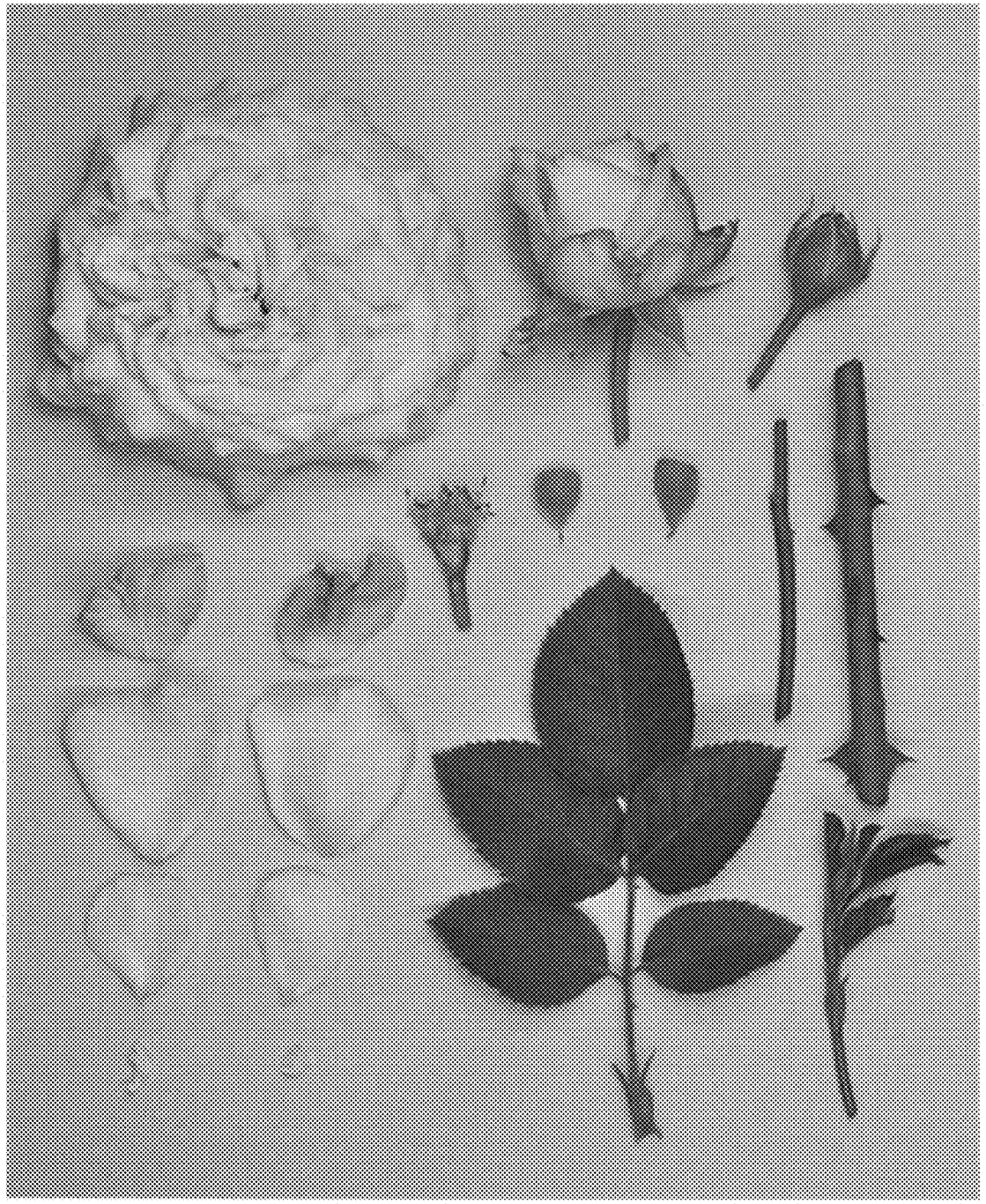

* * * * *